(12) United States Patent
Sookraj et al.

(10) Patent No.: US 10,781,156 B2
(45) Date of Patent: Sep. 22, 2020

(54) COMPOSITIONS FOR IMPROVED PRODUCTION OF ACRYLIC ACID

(71) Applicant: Novomer, Inc., Boston, MA (US)

(72) Inventors: Sadesh H. Sookraj, Cambridge, MA (US); Kyle Evan Sherry, Rochester, NY (US)

(73) Assignee: Novomer, Inc., Rochester, NY (US)

( * ) Notice: Subject to any disclaimer, the term of this patent is extended or adjusted under 35 U.S.C. 154(b) by 42 days.

(21) Appl. No.: 16/023,612

(22) Filed: Jun. 29, 2018

(65) Prior Publication Data
US 2019/0031592 A1 Jan. 31, 2019

Related U.S. Application Data

(63) Continuation-in-part of application No. 15/640,324, filed on Jun. 30, 2017.

(51) Int. Cl.
*C07C 51/377* (2006.01)
*C07C 51/09* (2006.01)
(Continued)

(52) U.S. Cl.
CPC ......... *C07C 51/377* (2013.01); *B01J 27/232* (2013.01); *B01J 31/0209* (2013.01);
(Continued)

(58) Field of Classification Search
CPC ....................................................... C08J 11/12
See application file for complete search history.

(56) References Cited

U.S. PATENT DOCUMENTS 2,361,036 A 10/1944 Kung
3,169,945 A 2/1965 Hostettler
(Continued)

FOREIGN PATENT DOCUMENTS

EP 0887334 B1 12/1998
WO 2011100608 A1 8/2011
(Continued)

OTHER PUBLICATIONS

Notification of Transmittal of the International Search Report and Written Opinion dated Oct. 9, 2018, issued in International Application No. PCT/US2018/040412 (13 pages).
(Continued)

*Primary Examiner* — Peter F Godenschwager
(74) *Attorney, Agent, or Firm* — Young Basile Hanlon & MacFarlane, P.C.

(57) ABSTRACT

The present invention is directed to compositions which may undergo thermolysis to produce a higher purity acrylic acid product. In preferred embodiments of the present invention, the compositions comprise polypropiolactone and one or more active salts. The one or more active salts may catalyze thermolysis of the polypropiolactone so that the polymer depolymerizes into acrylic acid monomers. Certain concentrations of the one or more active salts result in higher purity acrylic acid products of thermolysis. In certain preferred embodiments, the one or more active salts include an acrylate group which may decompose under thermolysis to provide acrylic acid and thus decrease the concentration of undesirable contaminants in the acrylic acid product. In certain preferred embodiment, the one or more active salts comprise sodium acrylate.

10 Claims, 3 Drawing Sheets

(51) Int. Cl.
B01J 27/232 (2006.01)
B01J 31/02 (2006.01)
C07C 57/04 (2006.01)
B01J 31/04 (2006.01)

(52) U.S. Cl.
CPC .......... B01J 31/0239 (2013.01); B01J 31/04 (2013.01); C07C 51/09 (2013.01); C07C 57/04 (2013.01)

(56) References Cited

U.S. PATENT DOCUMENTS

| | | | |
|---|---|---|---|
| 3,678,069 | A | 7/1972 | Busler |
| 3,954,854 | A | 5/1976 | Gehrmann |
| 4,317,926 | A | 3/1982 | Sato |
| 4,792,620 | A | 12/1988 | Paulik |
| 5,310,948 | A | 5/1994 | Drent |
| 5,359,081 | A | 10/1994 | Drent |
| 5,648,452 | A | 7/1997 | Schechtman |
| 6,133,402 | A | 10/2000 | Coates |
| 6,252,110 | B1 | 6/2001 | Uemura |
| 6,316,590 | B1 | 11/2001 | Coates |
| 6,538,101 | B2 | 3/2003 | Coates |
| 6,608,170 | B1 | 8/2003 | Coates |
| 6,852,865 | B2 | 2/2005 | Coates |
| 6,887,380 | B2 | 5/2005 | Lee |
| 7,420,064 | B2 | 9/2008 | Luinstra |
| 9,115,070 | B2 | 8/2015 | Pazicky |
| 10,065,914 | B1* | 9/2018 | Ruhl ............ C07C 57/04 |
| 2005/0014977 | A1 | 1/2005 | Drent |
| 2007/0161806 | A1 | 7/2007 | Preishuber-Pflugl |
| 2010/0150976 | A1* | 6/2010 | Schnitzler ............ A61K 8/0208 424/401 |
| 2014/0018574 | A1 | 1/2014 | Raith |
| 2014/0275575 | A1 | 9/2014 | Allen |
| 2015/0183708 | A1 | 7/2015 | Harris |
| 2017/0029352 | A1 | 2/2017 | Sookraj |

FOREIGN PATENT DOCUMENTS

| | | |
|---|---|---|
| WO | 2013063191 A1 | 5/2013 |
| WO | 2013126375 A1 | 8/2013 |
| WO | 2013185009 A1 | 12/2013 |
| WO | 2014004858 A1 | 1/2014 |
| WO | 2014008232 A2 | 1/2014 |
| WO | WO2016/130947 | 8/2016 |
| WO | WO2016/131003 | 8/2016 |
| WO | 2017023777 A9 | 2/2017 |
| WO | 2017023820 | 2/2017 |

OTHER PUBLICATIONS

Iwabuchi, Susumu, et al. "The Thermal Degradation of Poly(oxycarbonylethylene) (Poly-beta-propiolactone)" from Die Makromolekulare Chemie (1973) at pp. 59-72.
Notification of Transmittal of the International Search Report and Written Opinion dated Nov. 8, 2016, issued in International Application No. PCT/US2016/044772 (19 pages).
Notification of Transmittal of the International Search Report and Written Opinion dated Nov. 8, 2016, issued in International Application No. PCT/US2016/044927 (19 pages).
Sorrell, Thomas. Organic Chemistry, University Science Books, Sausalito, 1999.
Liu et al. Reducing the Formation of Six-Membered Ring Ester During Thermal Degradation of Biodegradable PHBV to Enhance its Thermal Stability. Polymer Degradation and Stability, 94 (2009) pp. 18-24.
Beta Elimination of Esters in Poly Lactones, Aug. 17, 2017.
Nguyen et al. Thermal Degradation of Poly(3-hydroxyalkanoates): Preparation of Well-Defined Oligomers. Biomacromolecules, 3 (2002) pp. 219-224.
JP 45-19281 Recovery of AA from dimer (Rus) (1). (Machine English translation attached.).
Kim et al. Effect of Metal Compounds on Thermal Degradation Behavior of Aliphatic Poly(hydroxyalkanoic acid)s. Polymer Degradation and Stability, 93 (2008) pp. 776-785.
Kim et al. Effects of Residual Metal Compounds and Chain-End Structure on Thermal Degradation of Poly(3-hydroxybutyric acid). Polymer Degradation and Stability, 91 (2006) pp. 769-777.
Zhu et al. Polymorphic Crystallization and Melting-Recrystallization Behavior of Poly(3-hydroxyproplonate). Macromolecules, 38 (2005) pp. 6455-6465.
Kim et al. Thermal Degradation Behavior of Poly(4-hydroxybutyric acid). Polymer Degradation and Stability, 91 (2006) pp. 2333-2341.
Varma-Nair et al. Heat Capacity and Other Thermodynamic Properties of Linear Macromolecules (1980).
Kopinke et al. Thermal Decomposition of Biodegradable Polyesters-I: Poly(beta-hydroxybutyric acid). Polymer Degradation and Stability, 52 (1996) pp. 25-38.
Abe. Thermal Degradation of Environmentally Degradable Poly(hydroxyalkanoic acid)s. Macromolecular Bioscience (2006) pp. 469-486.
Abe et al. Effects of Residual Zinc Compounds and Chain-End Structure on Thermal Degradation of Poly(epsilon-caprolactone). Biomacromolecules, 5 (2004) pp. 1480-1488.
Dunn. Synthesis of Poly(hydroxyalkanoates): Routes to Poly(3-hydroxybutyrate) and Poly(3-hydroxypropionate) from the Carbonylation and Ring-Opening Polymerization of Epoxides. Dissertation, Cornell University (2012).
Jacobi et al. Strukturuntersuchung von Polyestern durch direkten Abbau im Massenspektrometer, 4. Makromol. Chem., 179 (1978) pp. 429-436.
Kricheldorf et al. Strukturuntersuchung von Polyestern durch direkten Abbau im Massenspektrometer, 3. Makromol. Chem., 179 (1978) pp. 421-427.
Garozzo et al. Primary Thermal Decomposition Processes in Aliphatic Polyesters Investigated by Chemical Ionization Mass Spectrometry. Macromolecules, 19 (1986) pp. 1643-1649.
Gresham et al. Beta-Propiolactone I. Polymerization Reactions. vol. 70 (1948) pp. 998-999.
Gresham et al. Beta-Propiolactone II. Reactions with Salts of Inorganic Acids. vol. 70 (1948) pp. 999-1001.
Gresham et al. Beta-Propiolactone III. Reactions with Dithiocarbamic Acids, their Salts and Thiourea. vol. 70 (1948) pp. 1001-1002.
Gresham et al. Beta-Propiolactone IV. Reactions with Salts of Carboxylic Acids. vol. 70 (1948) pp. 1003-1004.
Gresham et al. Beta-Propiolactone V. Reaction with Alcohols. vol. 70 (1948) pp. 1004-1006.
Luderwald et al. Strukturuntersuchung von Polyestern durch direkten Abbau im Massenspektrometer, 2. Makromol. Chem., 177 (1976) pp. 2093-2111.
Norskov et al, Nature Chemistry, Towards the Computational Design of Solid Catalysts, 2009, 1, pp. 37-46 (Year: 2009).

* cited by examiner

COMPOSITIONS FOR IMPROVED PRODUCTION OF ACRYLIC ACID

CROSS-REFERENCES

The present application claims benefit from U.S. application Ser. No. 15/640,324, filed Jun. 30, 2017, which is hereby incorporated by reference in its entirety as if fully restated herein.

FIELD OF THE INVENTION

This invention generally relates to compositions for the improved production of acrylic acid through a thermolysis reaction. Specifically, embodiments of the present invention include compositions comprising poly-propiolactone and one or more active salt which may catalyze the thermolysis of polypropiolactone to produce acrylic acid. Advantageously, embodiments of the present invention may be more efficiently transported and stored and may provide higher purity acrylic acid products of thermolysis.

BACKGROUND OF THE INVENTION

Polypropiolactone, termed "PPL" for the purposes of this application, is a biodegradable polymer that can be useful material in many manufacturing and industrial applications. The physical and chemical characteristics of PPL provide for safer transportation and storage over extended periods of time with decreased quality concerns. PPL is also a useful precursor because the polymer may undergo a chemical process known as thermolysis to produce acrylic acid.

Generally, thermolysis is a chemical decomposition reaction caused by heat. Thermolysis of PPL may proceed by two known reactions. In one reaction, a PPL polymer with a chain length equal to (n) decomposes into a PPL polymer with a chain length (n-1) and a molecule of acrylic acid. In another reaction, a PPL polymer with a chain length (n) decomposes into a PPL polymer with a chain length (n-x) and a PPL polymer with a chain length (x), where (x) is greater than or equal to 2.

Under certain reaction conditions, acrylic acid may be susceptible to auto-polymerization. In one auto-polymerization reaction, a first molecule of acrylic acid is added to a second molecule of acrylic acid to form a di-acrylic acid ester, which is identical to a PPL polymer with a chain length of 2. There is no known inhibitor which will prevent the addition of one molecule of acrylic acid to another. However, the di-acrylic acid ester may readily undergo thermolysis and decompose back into two molecules of acrylic acid. In a second auto-polymerization reaction, multiple molecules of acrylic acid undergo radical polymerization to form larger chains of polyacrylic acid. These larger chains of polyacrylic acid are not likely to convert back into individual molecules of acrylic acid under thermolysis conditions.

Radical polymerization of acrylic acid may be limited with the use of certain known inhibitors. However, these radical polymerization inhibitors may be costly, inefficient, and/or difficult to source. Additionally, conventional thermolysis reactor systems may not efficiently thermolyze polypropiolactone or may not effectively produce acrylic acid vapor effluent. There exists a need for compositions for an intermediate which may be thermolyzed to produce higher purity acrylic acid products. The present invention satisfies this need by providing compositions comprising PPL and one or more active salt.

SUMMARY OF THE INVENTION

The present invention is directed to compositions comprising PPL and one or more active salt. Advantageously, embodiments of the present invention may be more easily transported and stored with decreased safety concerns and may provide higher purity acrylic acid products of thermolysis.

In preferred embodiments of the present invention, the compositions comprising PPL and one or more active salt may be a stable material that can be safely transported and stored for extended periods without the safety concerns or the quality declines attendant with shipping and storing acrylic acid. If acrylic acid is needed, then the compositions of the present invention may be readily decomposed in a thermolysis reaction vessel to produce higher purity acrylic acid. Therefore, certain embodiments the present invention enable access to acrylic acid in a safer and/or less expensive and/or highly configurable manner. In certain embodiments, the liberated acrylic acid is of a purity suitable for direct use in the manufacture of acrylic acid polymers such as SAPs.

In certain preferred embodiments, the compositions may comprise PPL as a liquid and/or solid and the PPL may have a varying chain length. In certain preferred embodiments, the PPL preferably may be present at a high concentration by weight. In some embodiments, the compositions may also include β-propiolactone and/or sodium acrylate. The β-propiolactone ("BPL") preferably may be present in the compositions at a lower concentration by weight. The sodium acrylate preferably may be present in the compositions at a lower concentration by weight.

While this disclosure is susceptible to various modifications and alternative forms, specific exemplary embodiments thereof have been shown by way of example in the drawings and have herein been described in detail. It should be understood, however, that there is no intent to limit the disclosure to the particular embodiments disclosed, but on the contrary, the intention is to cover all modifications, equivalents, and alternatives falling within the scope of the disclosure as defined by the appended claims.

BRIEF DESCRIPTION OF THE DRAWINGS

The present invention can be better understood by reading the following detailed description of certain preferred embodiments, reference being made to the accompanying drawings in which.

DETAILED DESCRIPTION OF EMBODIMENTS

Figure 1:
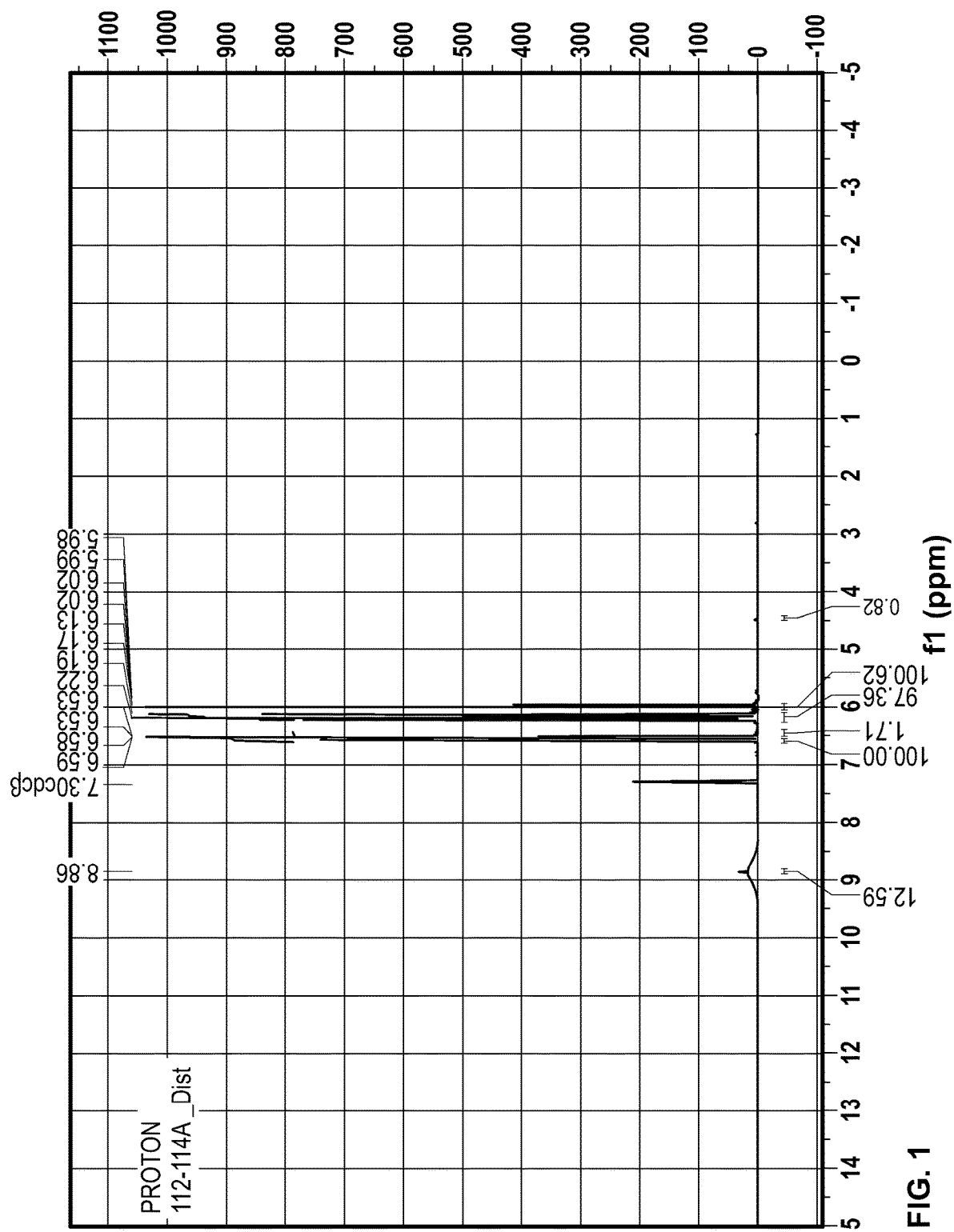
FIG. 1 illustrates an H NMR graph of an acrylic acid product formed from thermolysis of a composition of the present invention comprising one or more active salt having a concentration between 0.01% and 1% by weight.

The following description sets forth exemplary processes, parameters and the like. It should be recognized, however, that such description is not intended as a limitation on the scope of the present disclosure but is instead provided as a description of exemplary aspects.

The term "polymer", as used herein, refers to a molecule of high relative molecular mass, the structure of which comprises the multiple repetition of units derived, actually or conceptually, from molecules of low relative molecular mass. In some aspects, a polymer is comprised of only one monomer species. In some aspects, a polymer is a copolymer, terpolymer, heteropolymer, block copolymer, or tapered heteropolymer of one or more epoxides.

The terms bio-content and bio-based content mean biogenic carbon also known as bio-mass derived carbon, carbon waste streams, and carbon from municipal solid waste. In some variations, bio-content (also referred to as "bio-based content") can be determined based on the following:

Bio-content or Bio-based content=[Bio (Organic) Carbon]/[Total (Organic) Carbon] 100%, as determined by ASTM D6866 (Standard Test Methods for Determining the Bio-based (biogenic) Content of Solid, Liquid, and Gaseous Samples Using Radiocarbon Analysis).

As disclosed in US 20170002136 published on Jan. 5, 2017 and filed on Jun. 30, 2016, the ASTM D6866 method allows the determination of the bio-based content of materials using radiocarbon analysis by accelerator mass spectrometry, liquid scintillation counting, and isotope mass spectrometry. When nitrogen in the atmosphere is struck by an ultraviolet light produced neutron, it loses a proton and forms carbon that has a molecular weight of 14, which is radioactive. This 14C is immediately oxidized into carbon dioxide, and represents a small, but measurable fraction of atmospheric carbon. Atmospheric carbon dioxide is cycled by green plants to make organic molecules during photosynthesis. The cycle is completed when the green plants or other forms of life metabolize the organic molecules producing carbon dioxide which is then able to return back to the atmosphere. Virtually all forms of life on Earth depend on this green plant production of organic molecules to produce the chemical energy that facilitates growth and reproduction. Therefore, the 14C that exists in the atmosphere becomes part of all life forms and their biological products. These renewably based organic molecules that biodegrade to carbon dioxide do not contribute to global warming because no net increase of carbon is emitted to the atmosphere. In contrast, fossil fuel-based carbon does not have the signature radiocarbon ratio of atmospheric carbon dioxide. See WO 2009/155086, incorporated herein by reference.

The application of ASTM D6866 to derive a "bio-based content" is built on the same concepts as radiocarbon dating, but without use of the age equations. The analysis is performed by deriving a ratio of the amount of radiocarbon (14C) in an unknown sample to that of a modern reference standard. The ratio is reported as a percentage, with the units "pMC" (percent modern carbon). If the material being analyzed is a mixture of present day radiocarbon and fossil carbon (containing no radiocarbon), then the pMC value obtained correlates directly to the amount of bio-based material present in the sample. The modern reference standard used in radiocarbon dating is a NIST (National Institute of Standards and Technology) standard with a known radiocarbon content equivalent approximately to the year AD 1950. The year AD 1950 was chosen because it represented a time prior to thermonuclear weapons testing which introduced large amounts of excess radiocarbon into the atmosphere with each explosion (termed "bomb carbon"). The AD 1950 reference represents 100 pMC. "Bomb carbon" in the atmosphere reached almost twice normal levels in 1963 at the peak of testing and prior to the treaty halting the testing. Its distribution within the atmosphere has been approximated since its appearance, showing values that are greater than 100 pMC for plants and animals living since AD 1950. The distribution of bomb carbon has gradually decreased over time, with today's value being near 107.5 pMC. As a result, a fresh biomass material, such as corn, could result in a radiocarbon signature near 107.5 pMC.

Petroleum-based carbon does not have the signature radiocarbon ratio of atmospheric carbon dioxide. Research has noted that fossil fuels and petrochemicals have less than about 1 pMC, and typically less than about 0.1 pMC, for example, less than about 0.03 pMC. However, compounds derived entirely from renewable resources have at least about 95 percent modern carbon (pMC), they may have at least about 99 pMC, including about 100 pMC.

Combining fossil carbon with present day carbon into a material will result in a dilution of the present day pMC content. By presuming that 107.5 pMC represents present day bio-based materials and 0 pMC represents petroleum derivatives, the measured pMC value for that material will reflect the proportions of the two component types. A material derived 100% from present day biomass would give a radiocarbon signature near 107.5 pMC. If that material were diluted with 50% petroleum derivatives, it would give a radiocarbon signature near 54 pMC.

A bio-based content result is derived by assigning 100% equal to 107.5 pMC and 0% equal to 0 pMC. In this regard, a sample measuring 99 pMC will give an equivalent bio-based content result of 93%.

Assessment of the materials described herein according to the present embodiments is performed in accordance with ASTM D6866 revision 12 (i.e. ASTM D6866-12), the entirety of which is herein incorporated by reference. In some embodiments, the assessments are performed according to the procedures of Method B of ASTM-D6866-12. The mean values encompass an absolute range of 6% (plus and minus 3% on either side of the bio-based content value) to account for variations in end-component radiocarbon signatures. It is presumed that all materials are present day or fossil in origin and that the desired result is the amount of bio-based carbon "present" in the material, not the amount of bio-material "used" in the manufacturing process.

Other techniques for assessing the bio-based content of materials are described in U.S. Pat. Nos. 3,885,155, 4,427,884, 4,973,841, 5,438,194, and 5,661,299, and WO 2009/155086, each of which is incorporated herein by reference.

The term "acrylate" or "acrylates" as used herein refer to any acyl group having a vinyl group adjacent to the acyl carbonyl. The terms encompass mono-, di- and tri-substituted vinyl groups. Examples of acrylates include, but are not limited to: acrylate, methacrylate, ethacrylate, cinnamate (3-phenylacrylate), crotonate, tiglate, and senecioate.

As used herein, the term "catalyst" refers to a substance the presence of which increases the rate of a chemical reaction, while not being consumed or undergoing a permanent chemical change itself.

Renewable resources means a source of carbon and/or hydrogen obtained from biological life forms that can replenish itself in less than one hundred years.

Renewable carbon means carbon obtained from biological life forms that can replenish itself in less than one hundred years.

It should be understood that reference to "between" two values or parameters herein includes (and describes) aspects that include those two values or parameters per se. For example, description referring to "between x and y" includes description of "x" and "y" per se.

The mass fractions disclosed herein can be converted to wt % by multiplying by 100.

The present invention is directed to novel compositions which may undergo thermolysis to produce higher purity acrylic acid. The compositions of the present invention are comprised of PPL and one or more active salts. In certain embodiments, thermolysis may decompose the PPL to produce acrylic acid at a temperature greater than about 100° C., greater than about 150° C., greater than about 175° C., greater than about 200° C., or greater than about 220° C.

In preferred embodiments, the present invention is directed to compositions comprising PPL at a concentration at least about 90% by weight. More preferably, compositions of the present invention comprise PPL at a concentration of at least about 95% by weight. Most preferably, compositions of the present invention comprise PPL at a concentration of at least about 98% by weight. The compositions of the present invention preferably include PPL at a concentration less than about 100% by weight.

In certain embodiments, the PPL may be characterized as a liquid. In certain embodiments, such liquid PPL compositions have a higher percentage of relatively low-molecular weight polymer chains. In certain embodiments, the number average molecular weight (MN) of the PPL produced is between about 200 g/mol and about 10,000 g/mol. In certain embodiments, the MN of the PPL produced is less than about 5,000 g/mol, less than about 3,000 g/mol, less than about 2,500 g/mol, less than about 2,000 g/mol, less than about 1,500 g/mol, less than about 1,000 g/mol, or less than about 750 g/mol. In certain embodiments, the PPL produced comprises oligomers containing from about 2 to about 10 monomer units. In certain embodiments, such oligomers comprise cyclic oligomers. In certain embodiments, cyclic oligomers contain, on average about 2 monomer units, about 3 monomer units, about 4 monomer units, about 5 monomer units, about 6 monomer units, up to about 10 monomer units, or mixtures of two or more of these materials.

In certain embodiments, the PPL may be characterized as a solid. In certain embodiments, solid PPL compositions comprise a higher percentage of high molecular weight polymer chains. In certain embodiments, such high molecular PPL is characterized in that it has an M between about 10,000 g/mol and about 1,000,000 g/mol. In certain embodiments, high molecular PPL is characterized in that it has an M greater than about 10,000 g/mol, greater than about 20,000 g/mol, greater than about 50,000 g/mol, greater than about 70,000 g/mol, greater than about 100,000 g/mol, greater than about 150,000 g/mol, greater than about 200,000 g/mol, or greater than about 300,000 g/mol.

In preferred embodiments, the formation of the PPL includes carbonylation of ethylene oxide with carbon monoxide and a carbonylation catalyst to provide BPL which is then polymerized to provide PPL. In certain preferred embodiments, the BPL is not isolated from one reactor and polymerized in a second reactor, but rather is carbonylated and polymerized in situ to provide the PPL. In certain preferred embodiments, the BPL may be polymerized using an active salt as a catalyst. Advantageously, the novel compositions of the present invention may include residual active salt polymerization catalysts which are also thermolysis catalysts. In some embodiments, a portion of the active salt may be a residual from a polymerization reaction producing the polypropiolactone (PPL).

Polymerization of BPL to form PPL may be performed with various active salts for polymerization initiation including but not limited to alcohols, amines, polyols, polyamines, diols, metals (e.g., lithium, sodium, potassium, magnesium, calcium, zinc, aluminum, titanium, cobalt, etc.) metal oxides, carbonates of alkali- and alkaline earth metals, borates, and silicates. The polymerization process includes covalently incorporating such active salt polymerization initiators into a polymer chain. In certain embodiments, the present invention provides a solution to a potentially undesirable effect of this covalently bound initiator: namely, when the PPL is depolymerized to provide acrylic acid, the active salt polymerization initiator may also be liberated and may act as a contaminant in the acrylic acid produced. Therefore, in certain preferred embodiments, the step of polymerizing the BPL comprises contacting the BPL with a polymerization catalyst comprising an active salt including an acrylate. Polymers formed using an active salt including an acrylate as polymerization initiators have the added advantage that fewer non-acrylate materials arising from the bound initiator will contaminate the subsequent acrylic acid stream produced from thermolysis of the polymer. In certain preferred embodiments, the active salt comprises sodium acrylate and/or potassium acrylate.

In preferred embodiments, the present invention is directed to compositions comprising one or more active salt at a concentration of at least about 0.01% by weight. More preferably, compositions of the present invention comprise one or more active salt at a concentration of at least about 0.1% by weight. Most preferably, compositions of the present invention comprise one or more active salt at a concentration of at least about 1% by weight. The compositions of the present invention preferably include one or more active salt at a concentration of less than about 10% by weight.

Preferably, the one or more active salt comprises an alkali salt such as sodium carbonate and potassium carbonate. More preferably, the one or more active salt may be an acrylate salt such as sodium acrylate and potassium acrylate. Most preferably, the one or more active salt is sodium acrylate. In at least one embodiment, the one or more active salt comprises tert-butyl ammonium acrylate.

EXAMPLE 1

Conversion of Polypropriolactone (PPL) to Acrylic Acid by Using 0.01% and 1% by Weight of Active Metal Salt FIG. 1 illustrates the hydrogen nuclear magnetic resonance ("H NMR") graph of an acrylic acid product produced through thermolysis of a composition of the present invention comprising one or more active salts with a concentration between 0.01% and 1% by weight. The scheme for this reaction is shown below.

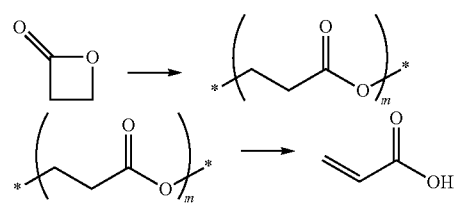

The acrylic acid product represented by the FIG. 1 illustration was produced using a lab-scale batch thermolysis process vessel comprising a two-necked round-bottom glass flask of 25 mL approximate internal volume. The thermolysis process vessel was equipped with an internal thermocouple and the top center opening was equipped with a separation chamber comprising a Vigreuxt™ column oriented coaxially (similar to Ace Glass™ item #6578-04), followed by an adapter with an additional thermocouple to monitor vapor temperature, followed by a water-cooled condenser, and finally a four-armed product receiver in a dry ice/acetone-cooled dewar. The thermolysis process vessel included a heater comprising a fabric heating mantle, the power to which was controlled by a temperature controller that receives feedback from the thermocouple inside the thermolysis process vessel. The thermolysis process vessel included a stirrer comprising a magnetic stir plate and a PTFE-coated stir bar.

A feed stream was introduced to the thermolysis process vessel comprising 5 mg phenothiazine and 6.660 g of PPL produced from ring-opening polymerization of solvent-free BPL in the presence of sodium acrylate at a concentration of 1 mol per 6,000 mol of BPL and phenothiazine at a concentration of 200 ppmw in BPL. The feed stream was heated in the thermolysis process vessel to 90° C. to melt and stirred. The thermolysis process vessel was brought under vacuum to an absolute pressure of approximately 400 torr, and the thermolysis process vessel temperature setpoint was set to 230° C. Internal reflux was observed inside the reaction flask within minutes.

The product sample 112-114A_Dist had a mass of 0.516 g, of a total 5.667 g total distillate collected. The HNMR analysis suggested an average acrylic acid content in 112-114A_Dist of 99.2%. The balance consisted of di-acrylic acid ester and traces of other PPL oligomers where n>2.

In certain embodiments, the polylactone product may undergo thermolysis continuously (e.g. in a fed batch reactor or other continuous flow reactor format) to form acrylic acid.

EXAMPLE 2

Figure 2:
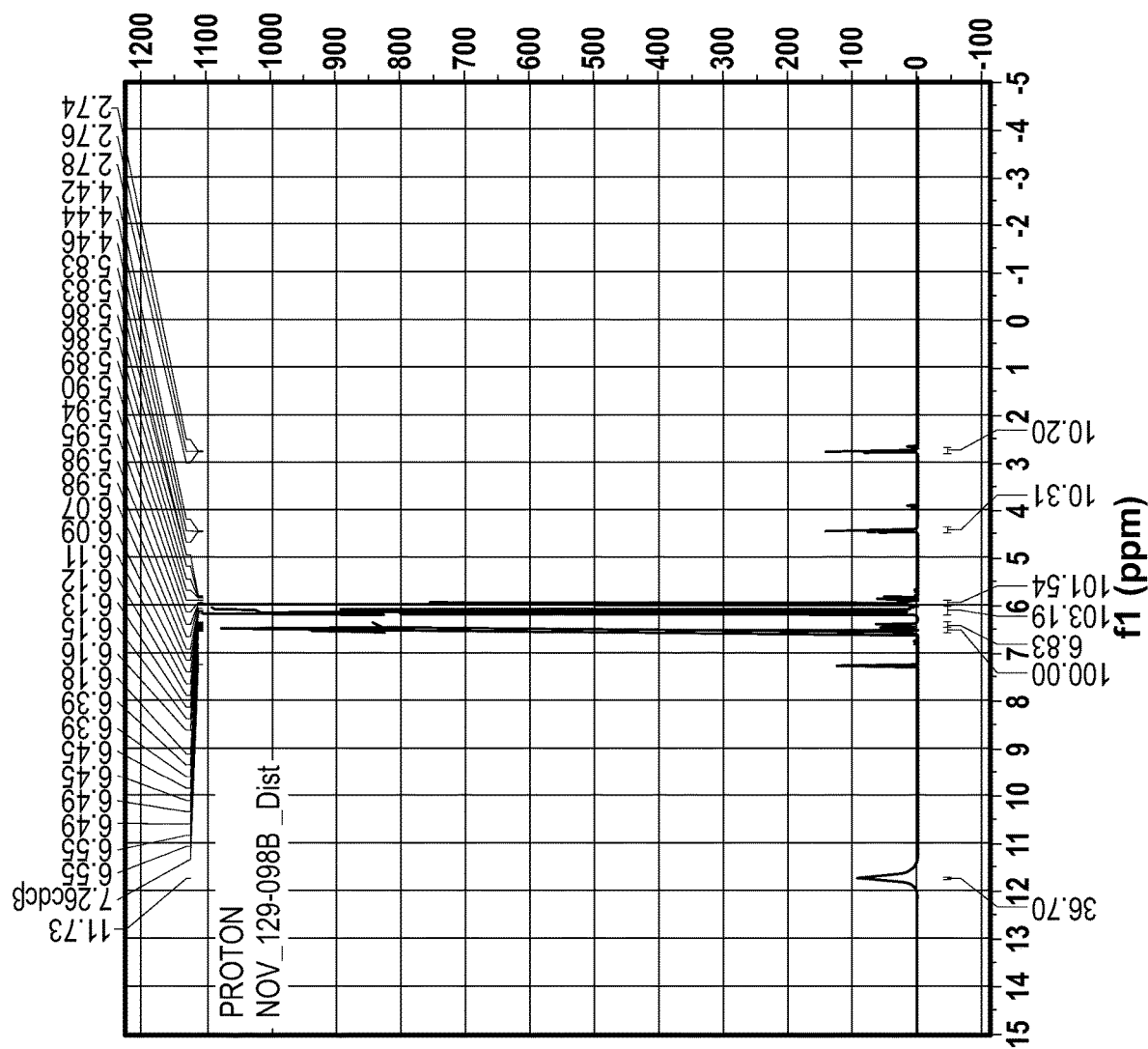
FIG. 2 illustrates an H NMR graph of an acrylic acid product formed from thermolysis of a composition of the present invention comprising one or more active salt having a concentration between 1% and 5% by weight.

Conversion of Polypropriolactone (PPL) to Acrylic Acid by Using 1% and 5% by Weight of Active Metal Salt FIG. 2 illustrates the hydrogen nuclear magnetic resonance graph of an acrylic acid product produced from thermolysis of a composition of the present invention comprising one or more active salt having a concentration between 1% and 5% by weight.

The acrylic acid product represented by the FIG. 2 illustration was produced using a lab-scale batch thermolysis process vessel comprising a two-necked round-bottom glass flask of 25 mL approximate internal volume. The thermolysis process vessel was equipped with an internal thermocouple and the top center opening of the thermolysis process vessel included a separation chamber comprising a short-path distillation apparatus including a short path still (similar to Ace Glass™ item #6554-06) with an additional thermocouple to monitor vapor temperature, followed by a water-cooled condenser, and finally a four-armed product receiver in a dry ice/acetone-cooled dewar. The thermolysis process vessel included a heater comprising a fabric heating mantle, the power to which was controlled by a temperature controller that receives feedback from the thermocouple inside the thermolysis process vessel. The thermolysis process vessel included a stirrer comprising a magnetic stir plate and a PTFE-coated stir bar.

A feed stream was introduced to the thermolysis process vessel comprising 90 mg dry sodium acrylate, 5 mg phenothiazine, and 4.995 g of PPL produced from ring-opening polymerization of solvent-free BPL in the presence of sodium acrylate at a concentration of 1 mol per 6,000 mol of BPL and phenothiazine at a concentration of 200 ppmw in BPL. The feed stream in the thermolysis process vessel was heated to 90° C. to melt and stirred. The thermolysis process vessel was brought under vacuum to an absolute pressure of approximately 700 torr, and the thermolysis process vessel temperature setpoint was set to 210° C. Internal reflux was observed inside the thermolysis process vessel within minutes and the thermolysis process vessel was held at 210° C. for 10 minutes.

The product sample 129-098B_Dist HNMR analysis suggested an average acrylic acid content in 129-098B_Dist of 90.7% by mass. The balance consists of di-acrylic acid ester and traces of other PPL oligomers where n>2.

EXAMPLE 3

Figure 3:
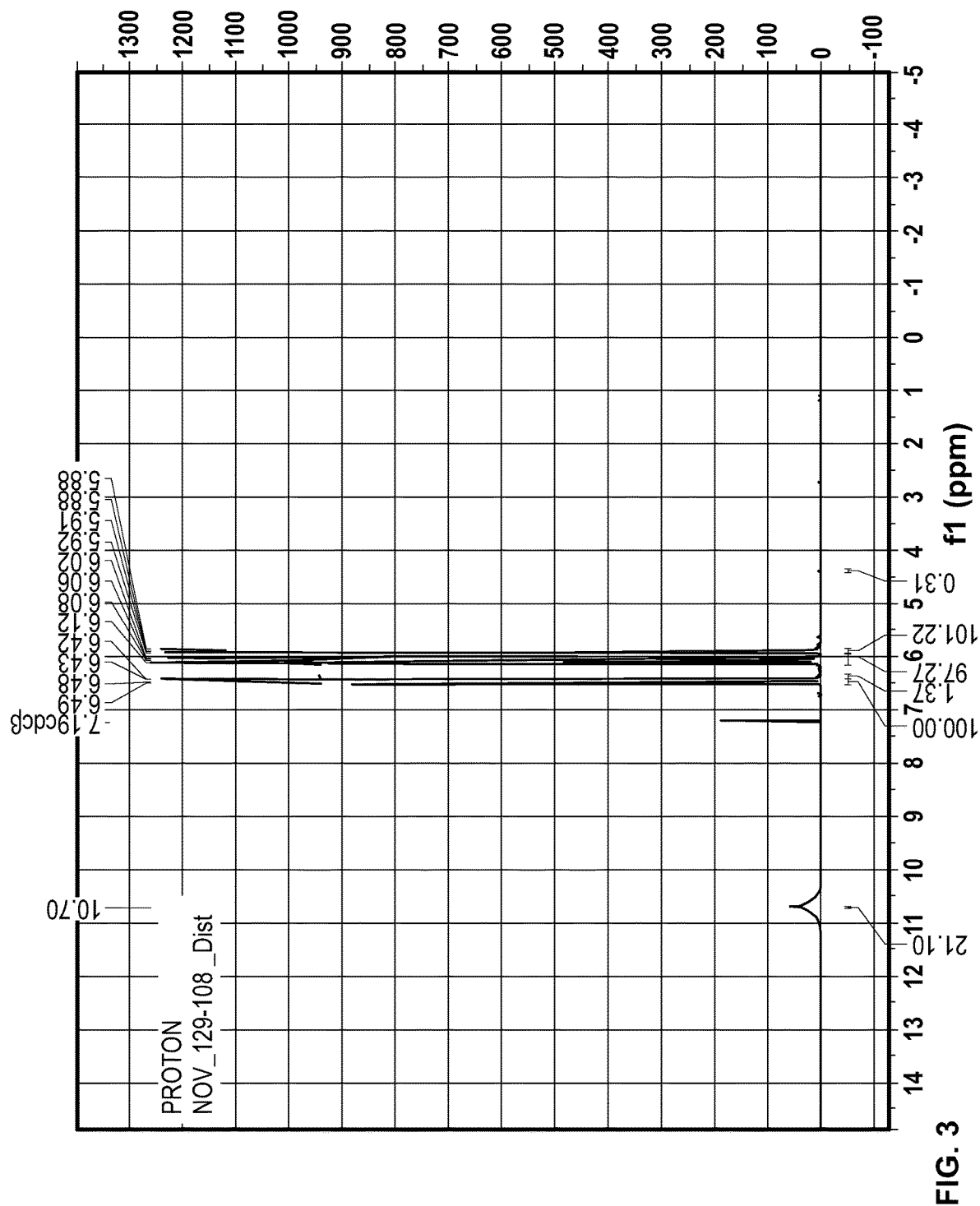
FIG. 3 illustrates an H NMR graph of an acrylic acid product formed from thermolysis of a composition of the present invention comprising one or more active salt having a concentration between 5% and 10% by weight.

Conversion of Polypropriolactone (PPL) to Acrylic Acid by Using 5% and 10% by Weight of Active Metal Salt FIG. 3 illustrates the hydrogen nuclear magnetic resonance graph of an acrylic acid product produced from thermolysis of a composition of the present invention comprising one or more active salt having a concentration between 5% and 10% by weight.

The acrylic acid product represented by the FIG. 3 illustration was produced using a lab-scale batch thermolysis process vessel comprising a two-necked round-bottom glass flask of 50 mL approximate internal volume. The thermolysis process vessel included an internal thermocouple and a separation chamber located at the top center opening in the thermolysis process vessel. The separation chamber comprised a distillation apparatus including two Vigreux™ columns in series oriented coaxially (each similar to Ace Glass™ item #6578-04), followed by an adapter with an additional thermocouple to monitor vapor temperature, followed by a water-cooled condenser, and finally a 50 mL round-bottom product receiver in a dry ice/acetone-cooled dewar. The thermolysis process vessel included a heater comprising a fabric heating mantle, the power to which was controlled by a temperature controller that received feedback from the thermocouple inside the thermolysis process vessel. The thermolysis process vessel included a stirrer comprising a magnetic stir plate and a PTFE-coated stir bar.

A feed stream was introduced to the thermolysis process vessel comprising 1000 mg dry sodium acrylate, 20 mg phenothiazine, and 19.162 g of PPL produced from ring-opening polymerization of solvent-free BPL in the presence of sodium acrylate at a concentration of 1 mol per 6,000 mol of BPL and phenothiazine at a concentration of 200 ppmw in BPL. The feed stream in the thermolysis process vessel was heated to 90° C. to melt and stirred. The thermolysis process vessel was brought under vacuum to an absolute pressure of approximately 90 torr, and the thermolysis process vessel temperature setpoint was set to 165° C. Internal reflux was observed inside the thermolysis process vessel within minutes. The thermolysis process vessel was held at 165° C. for 40 minutes.

The product sample 129-108_Dist HNMR analysis suggested an average acrylic acid content in 129-108_Dist of 99.7%. The balance consists of di-acrylic acid ester and traces of other PPL oligomers where n>2.

The embodiments described herein are not intended to be limited to the aspects shown, but are to be accorded the widest scope consistent with the principles and features disclosed herein.

What is claimed is:

1. A composition for producing a high purity acrylic acid thermolysis product, comprising:
   a. polypropiolactone, having a number average molecular weight of greater than about 750 g/mol and having a physical state that is a liquid or a solid; and
   b. one or more active salts for catalyzing thermolysis of the polypropiolactone when the composition undergoes thermolysis at thermolysis conditions, the one or more active salts chosen from the group including sodium carbonate and potassium carbonate.

2. The composition of claim 1, wherein a portion of the active salt is included in the polypropiolactone.

3. The composition of claim 1, wherein said composition has a polypropiolactone concentration of at least about 95% by weight.

4. The composition of claim 1, wherein said composition has polypropiolactone concentration of at least about 98% by weight.

5. The composition of claim 1, wherein the composition further comprises phenothiazine.

6. A composition for producing a high purity acrylic acid thermolysis product, comprising:
   a. polypropiolactone having with a concentration of at least about 95% by weight of the composition and a number average molecular weight between about 750 g/mol and about 10,000 g/mol; and
   b. one or more active salts for catalyzing thermolysis of said polypropiolactone when the composition undergoes thermolysis at thermolysis conditions, the one or more active salts chosen from the group including sodium carbonate and potassium carbonate.

7. The composition of claim 6, wherein a portion of the one or more active salts is part of the polypropiolactone.

8. The composition of claim 6, wherein said composition has polypropiolactone concentration of at least about 98% by weight.

9. A composition for producing a high purity acrylic acid thermolysis product, comprising:
   a. polypropiolactone with a concentration of at least about 98% by weight of the composition and a number average molecular weight greater than about 10,000 g/mol; and
   b. one or more active salts for catalyzing thermolysis of the polypropiolactone when the composition undergoes thermolysis at thermolysis conditions, the one or more active salts chosen from the group including sodium carbonate and potassium carbonate.

10. The composition of claim 9, wherein a portion of the one or more active salts is included in the polypropiolactone.

* * * * *